United States Patent
Lundberg et al.

(10) Patent No.: US 6,610,323 B1
(45) Date of Patent: Aug. 26, 2003

(54) ORAL PHARMACEUTICAL PULSED RELEASE DOSAGE FORM

(75) Inventors: Per Johan Lundberg, Mölndal; Brita Sjöblom, Hovås, both of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/555,720

(22) PCT Filed: Dec. 17, 1998

(86) PCT No.: PCT/SE98/02369

§ 371 (c)(1),
(2), (4) Date: Jun. 2, 2000

(87) PCT Pub. No.: WO99/32093

PCT Pub. Date: Jul. 1, 1999

(30) Foreign Application Priority Data

Dec. 22, 1997 (SE) ................................. 9704870

(51) Int. Cl.[7] ........................ A61K 9/22; A61K 9/26; A61K 9/54
(52) U.S. Cl. .................. 424/458; 424/457; 424/468; 424/469; 424/472; 424/474; 424/489; 424/490; 514/772.3; 514/778; 514/781
(58) Field of Search ..................... 424/489, 464, 424/451, 456, 468, 472, 490, 474, 469, 458

(56) References Cited

U.S. PATENT DOCUMENTS

| | | | |
|---|---|---|---|
| 4,786,505 A | 11/1988 | Lovgren et al. | 424/468 |
| 4,853,230 A | 8/1989 | Lovgren et al. | 424/466 |
| 5,229,131 A | 7/1993 | Amidon et al. | |
| 5,330,982 A | 7/1994 | Tyers | 514/214 |
| 5,567,441 A | 10/1996 | Chen | 424/464 |
| 5,753,265 A | 5/1998 | Bergstrand et al. | 424/474 |
| 5,817,338 A | 10/1998 | Bergstrand et al. | 424/468 |
| 5,945,124 A | 8/1999 | Sachs et al. | 414/472 |
| 6,068,856 A | 5/2000 | Sachs et al. | 424/474 |
| 6,132,768 A | 10/2000 | Sachs et al. | 424/458 |
| 6,136,344 A | 10/2000 | Depui et al. | 424/470 |
| 6,274,173 B1 | 8/2001 | Sachs et al. | 424/480 |

FOREIGN PATENT DOCUMENTS

| | | |
|---|---|---|
| EP | 0005129 | 10/1979 |
| EP | 0124495 | 11/1984 |
| EP | 0166287 | 1/1986 |
| EP | 0174726 | 3/1986 |
| EP | 0384642 | 8/1990 |
| EP | 0384646 | 8/1990 |
| EP | 0629398 | 12/1994 |
| GB | 2163747 | 3/1986 |
| WO | 9427988 | 12/1994 |
| WO | 9501783 | 1/1995 |
| WO | 9501977 | 1/1995 |
| WO | 9601623 | 1/1996 |
| WO | 9601624 | 1/1996 |
| WO | 9702020 | 1/1997 |
| WO | 9702021 | 1/1997 |
| WO | 9748380 | 12/1997 |

OTHER PUBLICATIONS

U.S. application No. 08/945,425, Cederberg et al., filed Oct. 21, 1997.

(List continued on next page.)

*Primary Examiner*—James M. Spear
(74) *Attorney, Agent, or Firm*—White & Case LLP

(57) ABSTRACT

An enteric coated pharmaceutical dosage form comprising an $H^+,K^+$-ATPase inhibitor is disclosed. The dosage form comprises at least two portions of the $H^+,K^+$-ATPase inhibitor to be released in at least two consecutive pulses. The dosage form has at least one fraction with a pulsed delayed release and another fraction with instant release of the $H^+,K^+$-ATPase inhibitor. The portions are released in time by from 0.5 and up to 12 hours interval, preferably by from 0.5 and up to 8 hours, and more preferably by from 0.5 and up to 4 hours interval. The dosage form is intended for once daily administration.

37 Claims, 3 Drawing Sheets

OTHER PUBLICATIONS

U.S. application No. 09/555,744, Karehill et al., filed Jan. 15, 1999.

Drugs and the gastrointestinal tract, The Pharmaceutical Journal (Jul. 27, 1991) pp. 137–139.

A new ibuprofen pulsed release oral dosage form, Columbo, P. et al., Drug Development and Industrial Pharmacy (1989) vol. 15, pp. 2583–2596.

Delayed release systems (DRS) based on a retarding swellable hydrophilic coating, Gazzaniga, A. and Giordano, F. (1993) Proceed. 12$^{th}$ Pharm. Int. Techn. Conf., vol. 1, pp. 400–408.

In vivo evaluation of oral Chronotopic® system for time and site specific delivery in the GI tract, Gazzaniga, A. et al. (1996) Proceed. Intern. Symp. Control. Rel. Bioact. Mater., Controlled Release Society, Inc., pp. 571–572.

Scand. J. Gastroenterol., Lind et al., 1986, 137–138.

Scand. J. Gastroenterol., Lind et al. 1988, 23, 1259–1266.

Remington's Pharmaceutical Sciences, John E. Hoover, 1975, p. 702.

Aulton, M.E. (Churchill Livingstone Ed.), Pharmaceutics-:The Science of Dosage Form Design, (1988) pp. 316–321.

Blum, A.L., "Perspektiven der Therapie mit Protonenpumpenblockern (PP–Blocker)", *Gastroenterol* (Suppl 33:32–40.

Gut, Lind et al., 1983, 270–276.

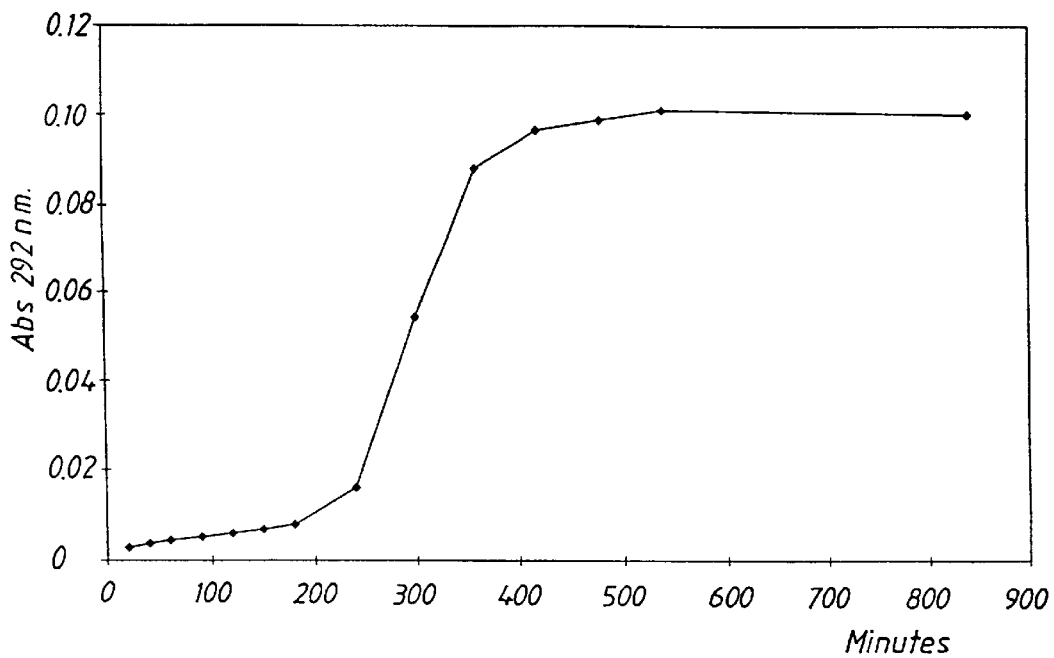
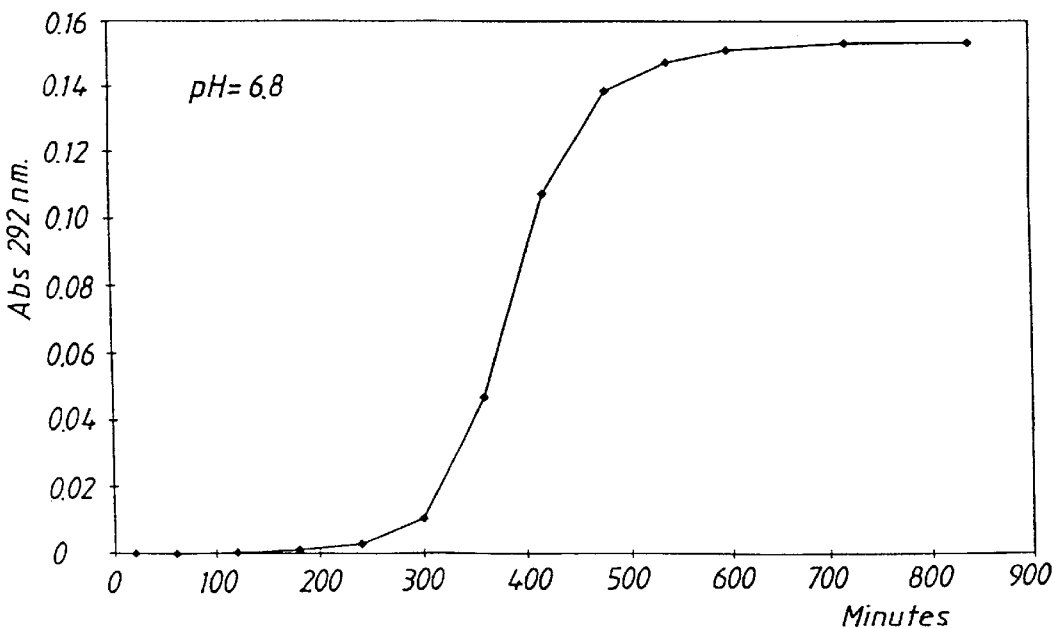

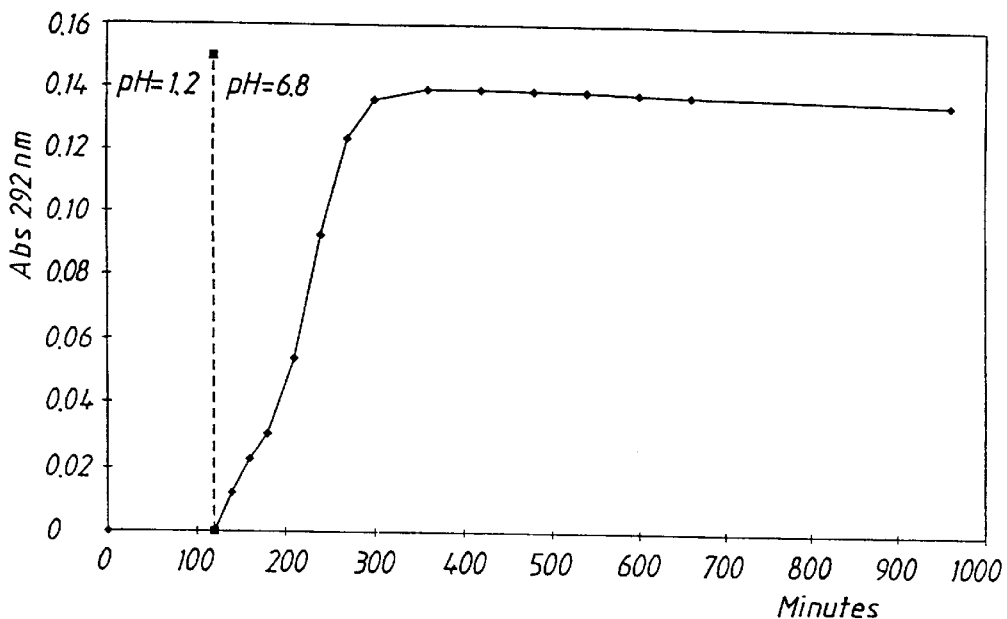
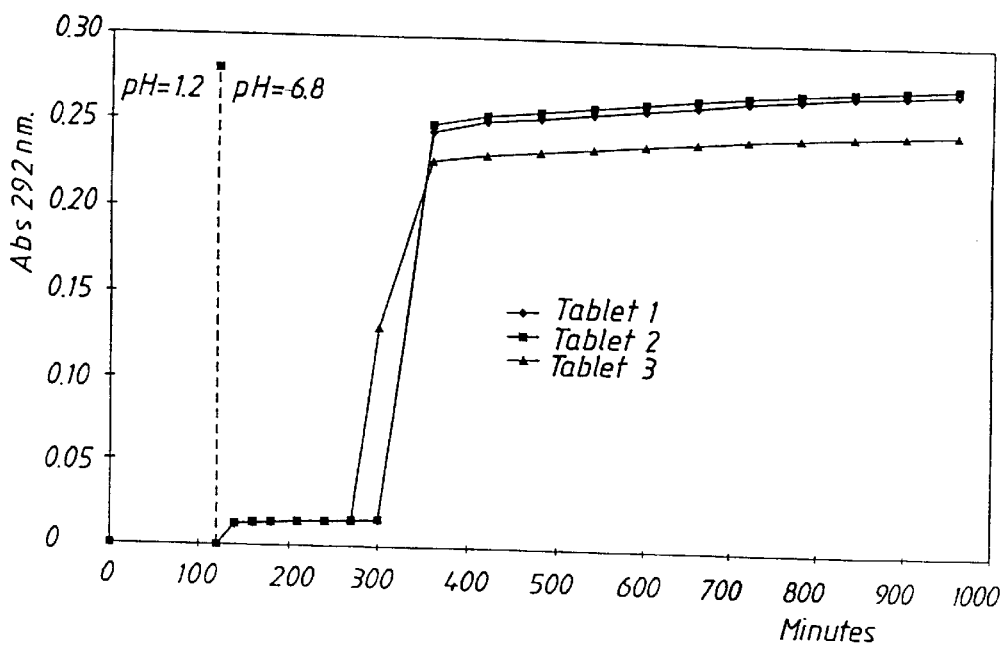

US 6,610,323 B1

ORAL PHARMACEUTICAL PULSED RELEASE DOSAGE FORM

This application is a 371 of PCT/SE98/02369 filed Dec. 18, 1998.

FIELD OF THE INVENTION

The present invention is related to new oral pharmaceutical dosage forms which comprise a proton pump inhibitor, i.e. a $H^+,K^+$-ATPase inhibitor. The new dosage forms are enteric coated formulations which provide a discontinuous pattern of two or more discrete release pulses of the $H^+,K^+$-ATPase inhibitor in the small and/or large intestines. The pulses are separated in time by from 0.5 and up to 12 hours, they are preferably separated by from 0.5 and up to 6 hours, and more preferably from 0.5 and up to 4 hours. Furthermore, the present invention refers to the manufacture of such pulsed delayed release pharmaceutical formulations, and their use in medicine.

BACKGROUND OF THE INVENTION AND PRIOR ART

Acid labile $H^+,K^+$-ATPase inhibitors also named as gastric proton pump inhibitors are for instance compounds known under the generic names omeprazole, lansoprazole, pantoprazole, rabeprazole and leminoprazole. Some of these compounds are disclosed in EP-A1-0005129, EP-A1-124495, WO 94/27988, EP-A1-174726, EP-A1-166287 and GB 2163747.

These pharmaceutical substances are useful for inhibiting gastric acid secretion in mammals including man by controlling gastric acid secretion at the final step of the acid secretory pathway and thus reduce basal and stimulated gastric acid secretion irrespective of stimulus. In a more general sense, they may be used for prevention and treatment of gastric-acid related diseases in mammals and man, including e.g. reflux oesophagitis, gastritis, duodenitis, gastric ulcer, duodenal ulcer and Zollinger-Ellison syndrome. Furthermore, they may be used for treatment of other gastrointestinal disorders where gastric acid inhibitory effect is desirable e.g. in patients on NSAID therapy, in patients with Non Ulcer Dyspepsia, and in patients with symptomatic gastro-oesophageal reflux disease (GORD). They may also be used in patients in intensive care situations, in patients with acute upper gastrointestinal bleeding, pre-and post-operatively to prevent aspiration of gastric acid and to prevent and treat stress ulceration. Further, they may be useful in the treatment of psoriasis as well as in the treatment of Helicobacter infections and diseases related to these.

Therapeutic control of gastric acid secretion is fundamental in all these disease, but the degree and duration of acid inhibition required for optimal clinical effect is not fully understood.

It has been proposed by the Applicant in WO97/48380, (published Dec. 24, 1997 i.e. after the priority date of the instant application,) that an administration regimen that gives blood plasma levels extending from 2–12 hours (by any of several means) will result in a larger fraction of proton pumps being inhibited. Thus, an extended blood plasma level 15 should result in more effective inhibition of acid secretion resulting in improved efficacy in GORD, more rapid healing of gastric ulcer and improved eradication of *H. Pylori*. The present invention provides pharmaceutically dosage forms which achieve such extended plasma levels by releasing the drug in two or more separate pulses.

A pharmaceutical dosage form of omeprazole or any other proton pump inhibitor is best protected from contact with acidic gastric juice by an enteric coating layer. In U.S. Pat. Nos. 4,786,505 and 4,853,230 such enteric coated preparations are described. These preparations have a core comprising an alkaline salt of the drug or a core comprising the drug together with an alkaline reacting compound. The core is coated with a water soluble or in water rapidly disintegrating separating layer and then with an enteric coating layer. WO 96/01623 and WO 96/01624 describe tableted dosage forms of omeprazole and other proton pump inhibitors, wherein enteric coating layered pellets are compressed into a multiple unit tableted dosage form. It is essential in these tableted formulations that the enteric coating layer can withstand the compression forces. None of these by the Applicant previously described formulations gave a dissolution of two or more pulses separated in time, i.e. in the meaning of pulsed release of the proton pump inhibitor which resulted in an extended blood plasma profile.

There are different technologies and pharmaceutical formulations described in the prior art which aim at a delayed release of an administered drug. Such pharmaceutical formulations are for instance formulations providing different lag times, constructions based on osmotic differences, slow-eroding/dissolving layers, time controlled explosion systems or any combinations thereof. In the following discussion some of these principles are described.

Gazzaniga et al (Proceed. $12^{th}$ Pharm. Int. Techn. Conf., 1993, 1, 400–8.) described tablets which were spray-coated or press-coated with HPMC layers to obtain delayed release preparations of ketoprofen or verapamil. The HPMC layer may also contain an insoluble filler. Gazzaniga et al have also described press-coated tablets containing antipyrine with HPMC layers to obtain delayed release, having an outer enteric coating comprising Eudragit L30D applied thereon. (Proc. Inter. Symp. Control. Rel. Bioact. Mater. 1996, 23, 571–2.)

EP-A1-0629398 describes a dosage form comprising a drug and an organic acid in a core surrounded by a film that controls the start of release, and further covered by an enteric coating layer. This dosage form is not suitable for substances that are sensitive to acidic degradation as the core comprises an organic acid.

Osmotic systems are described by Fox ("Colon-Targeted Osmotic System for Oral delivery of Peptides and Proteins", In; Oral Delivery of Proteins, Peptides and other Biopharmaceutical Agents; Proceedings Technology Management Group, Wakefield, Mass., USA, September 1991). A colon release system, OROS-CT, is used to obtain delayed extended release after a lag time. The dosage form had an enteric coating which dissolved in the small intestines, the drug release started after a desired lag time and the release was maintained during some hours.

EP 0384642 and EP 0384646 (as well as Pharm. J., Jul. 27, 1991 pp.137–9) introduced the PULSINCAP® dosage form both for enteric coated system and non-enteric coated system. The system comprises a capsule composed of a water insoluble body and a water soluble cap. The drug formulation was contained within the capsule body and sealed within this region by means of a hydrogel plug.

Conte et al (Drug Development and Industrial Pharmacy, 1989, vol 15, pp. 2583–96) described a three-layer tablet giving a double pulse system suitable for ibuprofen. The first layer contained a rapidly releasing formulation, and was separated from the layer comprising the second dose by a swellable polymeric barrier layer. The second dose was coated with an impermeable film of ethyl cellulose. This construction releases the drug in an acidic medium.

A dosage form for diltiazem was described in U.S. Pat. No. 5,567,441 comprising a mixture of one fraction of enteric coated pellets with slow release and another fraction of delayed pulse release membrane coated pellets. The latter fraction of pellets were not enteric coated. Such a dosage form will not be suitable for acidic sensitive drugs such as omeprazole or the like. There are two newly published patent applications which propose controlled release formulations comprising a proton pump inhibitor, i.e. in WO 97/02020 a dosage form for pantoprazole in combination with an antibacterial substance is proposed. At least a part of the pantoprazole dose shall be in slow-release form with a continuous release of pantoprazole over time. The preparation has one intermediate layer which will remain intact as a layer and is releasing the dose of pantoprazole continuously so as a pantoprazole plasma level persists as long as possible. WO 97/02021 discusses a very similar dosage form of a reversible proton pump inhibitor in combination with an antibacterial substance.

BRIEF DESCRIPTION OF THE DRAWINGS

FIGS. 1–5 show graphs illustrating the dissolution profiles for some of the inventive pharmaceutical formulations prepared in the examples. The graphs show the released amount of substance with respect to time. The amount of released substance is identified by registration of the absorbance at 292 nm in a buffer solution.

FIG. 1 shows the dissolution profile for single dose layered pellets prepared in Example 1.

FIG. 2 shows the dissolution profile for single dose layered pellets prepared in Example 2.

FIG. 3 shows the dissolution profile for single dose layered pellets prepared in Example 3.

FIG. 4 shows the dissolution profile for single dose layered tablets prepared in Example 5.

FIG. 5 shows the dissolution profile for multiple dose layered tablets prepared in Example 6.

SUMMARY OF THE INVENTION

Figure 5:
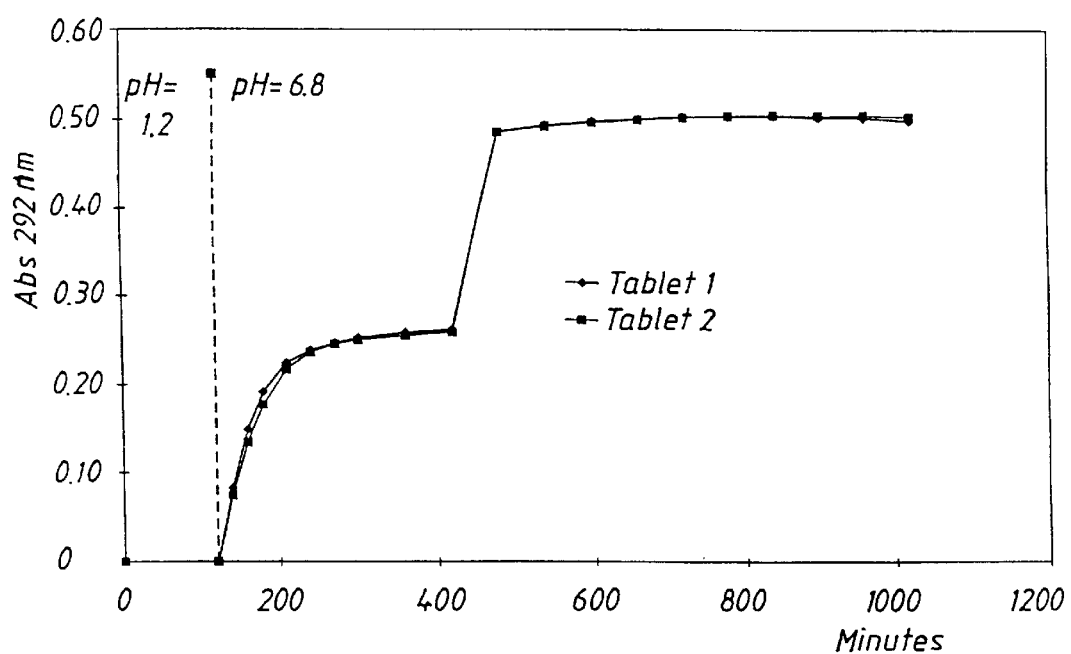

The therapeutic effect of omeprazole and similar substances may be improved by providing an extended plasma profile by once daily administration of a dosage form. The present invention obtains such an extended plasma profile by a pharmaceutical dosage form capable of releasing the drug in discrete pulses separated in time, i.e. a dosage form with a discontinuous release pattern. The present invention provides such dosage forms comprising an acid susceptible $H^+K^+$-ATPase inhibitor, such as omeprazole or any other proton pump inhibitor. A specific problem is that the pharmaceutical dosage forms suitable for a $H^+K^+$-ATPase inhibitor must fulfill certain requirement with respect to gastric acid resistance for enteric coated articles specified in the US Pharmacopeia (Edition 23).

According to one aspect of the invention the extended plasma profile of a proton pump inhibitor is provided by once daily administration of a dosage form which, in the small and/or large intestines (but not in the stomach), releases the proton pump inhibitor in two or more discrete pulses separated in time by from 0.5 up to 12 hours, preferably separated in time by from 0.5 and up to 8 hours, and more preferably by from 0.5 and up to 4 hours.

According to another aspect of the invention a discontinuous release pattern of the proton pump inhibitor by once daily administration of a dosage form is provided wherein a part of the dosage form gives a pulsed delayed release, and other parts of the dosage form release the proton pump inhibitor instantly. The dosage form provides at least two consecutive pulses for release of substance. The pulses should be separated in time by from 0.5 and up to 12 hours, preferably by from 0.5 and up to 8 hours, and more preferably by from 0.5 and up to 4 hours interval.

The present pulsed release formulations show an improved patient compliance over an administration regimen comprising consecutive administration of two or more unit doses within specified time intervals.

DETAILED DESCRIPTION OF THE INVENTION

Active Substance

Compounds of interest for the novel pharmaceutical formulations according to the present invention are compounds of the general formula I, an alkaline salt thereof, one of the single enantiomers thereof or an alkaline salt of one of the enantiomers

wherein
Het$_1$ is

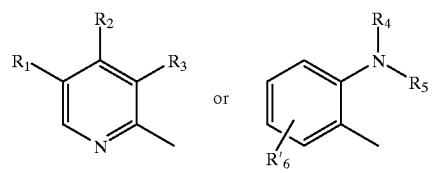

Het$_2$ is

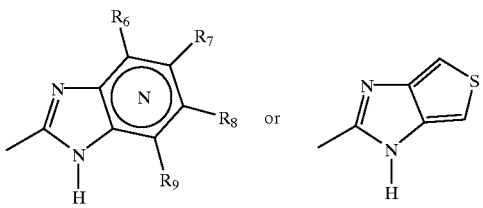

X=

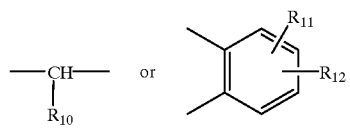

wherein
N in the benzimidazole moiety means that one of the ring carbon atoms substituted by R$_6$–R$_9$ optionally may be exchanged for a nitrogen atom without any substituents;

R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

$R_4$ and $R_5$ are the same or different and selected from hydrogen, alkyl and arylalkyl;

$R_6'$ is hydrogen, halogen, trifluoromethyl, alkyl or alkoxy;

$R_6$–$R_9$ are the same or different and selected from hydrogen, alkyl, alkoxy, halogen, haloalkoxy, alkylcarbonyl, alkoxycarbonyl, oxazolinyl, and trifluoroalkyl, or adjacent groups $R_6$–$R_9$ form ring structures which may be further substituted;

$R_{10}$ is hydrogen or forms an alkylene chain together with $R_3$ and $R_{11}$ and $R_{12}$ are the same or different and selected from hydrogen, halogen or alkyl.

Examples of specifically interesting compounds according to formula I are (Ia)

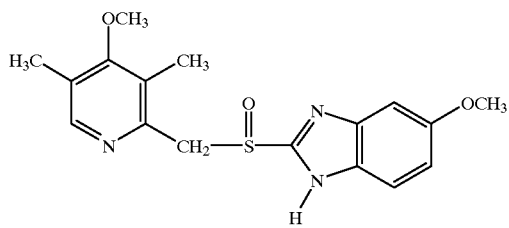

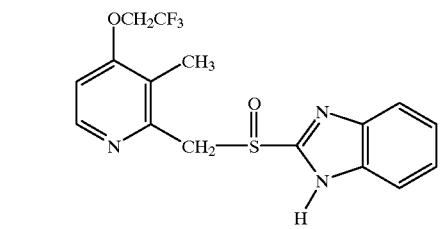

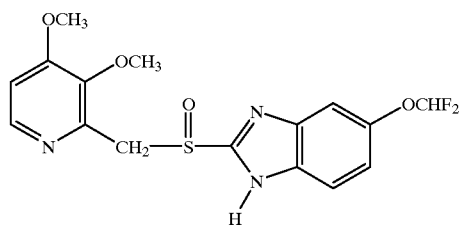

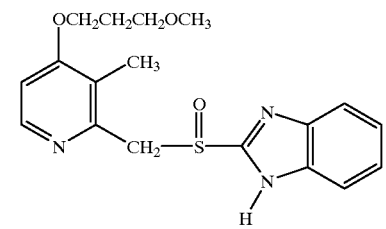

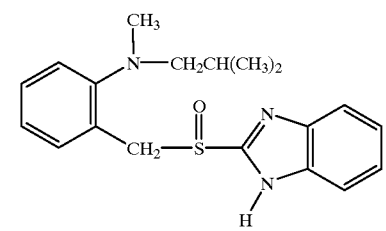

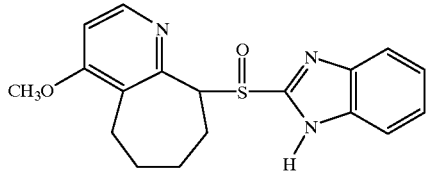

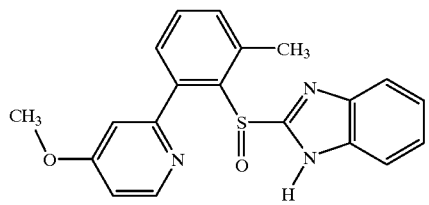

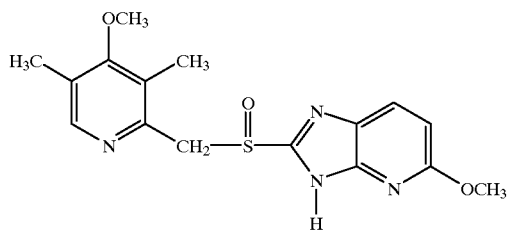

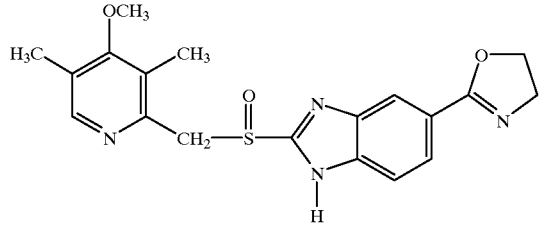

The compound suitable to be used in the pulsed release formulations according to the present invention may be used in neutral form or in the form of an alkaline salt, such as for instance the $Mg^{2+}$, $Ca^{2+}$, $Na^+$ or $K^+$ salts, preferably the $Mg^{2+}$ salts. The compounds may also be used in the form of one of its single enantiomers or an alkaline salt of the single enantiomer.

Especially preferred compounds for the oral pharmaceutical preparation according to the present invention are omeprazole, a magnesium salt of omeprazole or a magnesium salt of the (−)-enantiomer of omeprazole. Omeprazole and related substances as well as their preparations are described in EP 5129, EP 124 495, WO 95/01977, WO 94/27988 hereby incorporated as a whole by reference.

The above compounds are susceptible to degradation/transformation in acidic and neutral media. Generally, the degradation is catalyzed by acidic reacting compounds and the active compounds are stabilized with alkaline reacting compounds. There are different enteric coating layered preparations comprising omeprazole as well as other proton pump inhibitors described in the prior art, see for instance U.S. Pat. No. 4,853,230, WO 95/ 01783, and WO 96/01623. Especially, the latter describes alternative manufacturing methods for the preparation of enteric coating layered pellets comprising omeprazole and similar compounds.

The dosage forms according to the invention provide at least a part of the dose with a pulsed delayed release of the drug and another part of the formulation with rapid or instant release. The instant and pulsed delayed release of the drug can be achieved according to different principles, such as by single dose layered pellets or tablets, by multiple dose layered pellets or tablets, or by two or more different fractions of single or multiple dose layered pellets or tablets, optionally in combination with pellets or tablets having instant release.

Multiple dose layered pellets, or two or more different populations of single or multiple dose layered pellets prepared according to any of the below described principles, are filled into a capsule or together with tablet excipients compressed into a multiple unit tablet. Alternatively, a multiple dose layered tablet may be prepared.

Single Dose Layered Pellets or Tablets

According to one aspect of the invention, pellets or tablets giving one single delayed release pulse of the drug are prepared. The single dose layered pellets or tablets may be constructed as to comprise the following parts:

a core material, optionally layered on a seed/sphere, the core material comprising the drug together with a water swellable substance, and optionally pharmaceutically acceptable excipients, and the core material being free from acidic compounds, and thereupon the following sequence of layers:

a surrounding lag time controlling layer, and finally an enteric coating layer positioned to cover the lag time controlling layer.

According to an alternative aspect of the invention, it is also possible to construct the layered pellets or tablets as to comprise the following parts:

a core material, optionally layered on a seed/sphere, the core material comprises the drug optionally together with pharmaceutically acceptable excipients, and t he core material is being free from acidic compounds, and thereupon the following sequence of layers:

a surrounding layer comprising a water swellable substance, and thereupon a surrounding lag time controlling layer, and finally an enteric coating layer positioned to cover the lag time controlling layer.

Multiple Dose Layered Pellets or Tablets

According to another aspect of the invention, multiple dose layered pellets or tablets giving two or more delayed release pulses of the drug are prepared. These pellets or tablets may be constructed as to comprise the following parts:

a core material (I), optionally layered on a seed/sphere, the core material comprises the drug together with a water swellable substance, and optionally pharmaceutically acceptable excipients, and the core material is being free from acidic compounds, and thereupon the following sequence of layers:

a surrounding lag time controlling layer (II), and final a layer (III) comprising the drug optionally together with a water swellable substance, and/or pharmaceutically acceptable excipients; the layer is being free from acidic compounds, and optionally a separating layer (IV) which is water-soluble or in water rapidly disintegrating, wherein the layers II and III and the optional layer IV may appear in repeated sequences (in this order) and each set of layers (II+III) gives an additional single pulse of the drug. The dosage form is finally covered by an outer enteric coating layer (V).

Thus, a three-pulsed delayed release pellet or tablet could be constructed as having the following sequence of layers; I+II+III+II+III+an optional layer IV, and the prescribed outer enteric coating layer (V).

According to an alternative aspect of the invention, the multiple dose layered pellets or tablets may also be constructed with the following parts:

a core material (I), optionally layered on a seed/sphere, the core material comprises the drug optionally together with pharmaceutically acceptable excipients, and the core material is being free from acidic compounds, and thereupon the following sequence of layers:

a surrounding layer (II) comprising a water swellable substance, followed by a surrounding lag time controlling layer (III) and a layer (IV) comprising the drug optionally together with pharmaceutically acceptable excipients; the layer is being free from acidic compounds, and optionally a separating layer (V) which is water-soluble or in water rapidly disintegrating, wherein the layers II, III, IV and the optional layer V may appear in repeated sequences (in this order) and each set of layers (II+III+IV) gives an additional single pulse of the drug. The dosage form is covered by an outer enteric coating layer (VI).

Thus, a three-pulsed pellet or tablet could be constructed as having the following sequence of layers; I+II+III+IV+II+III+IV+an optional layer V, and the prescribed outer enteric coating layer (VI).

The core material comprising the active drug can be prepared either by coating layering the drug onto a seed, such as for instance sugar spheres, or by extrusion/spheronization of a mixture comprising the drug and pharmaceutically acceptable excipients. It is also possible to prepare the core material by using tablet technology, i.e. compression of drug granules and optionally pharmaceutically acceptable excipients into a tablet core.

For pellets of the two types, i.e. single or multiple dose pellets, which have the drug deposited onto a seed/sphere by layering, it is also possible to have an optional layer comprising a water swellable substance beneath the drug containing layer in the core material.

The prepared core material is used for further processing. Different techniques to prepare the core material for pellets or tablets are described below.

Core Material

The core material for the individual pellets or tablets can be constituted according to different principles. A seed/sphere layered with active substance, the active substance optionally mixed with a water swellable substance and/or a pharmaceutically acceptable excipient, can be used as core material for the further processing. The core material is free from acidic compound except that the active substance as such might be slightly acidic. The micro environment around the acid susceptible $H^+K^+$-ATPase inhibitor should preferable be not less than pH=7, and more preferably not less than pH=8 when water is absorbed to the core material mixture or when water is added in small amount to the mixture.

The seeds/spheres can be water insoluble and comprise different oxides, celluloses, organic polymers and other materials, alone or in mixtures, or be water soluble and comprise different inorganic salts, sugars and other materials, alone or in mixtures. Further, the seeds/spheres may comprise active substance in the form of crystals, agglomerates, compacts etc. The size of the seeds may vary between approximately 0.1 and 2 mm. The seeds layered with active substance are produced either by powder or solution/suspension layering using for instance granulating or spray coating/layering equipment.

Before the seeds are layered, the active substance may be mixed with further components to obtain preferred handling and processing properties and a suitable concentration of the active substance in the final mixture.

Such components can be binders, surfactants, fillers, disintegrating agents, alkaline additives or other pharmaceutically acceptable ingredients, alone or in mixtures. The binders are for example celluloses such as hydroxypropyl methylcellulose, methylcellulose, hydroxypropyl cellulose and carboxymethyl-cellulose sodium, polyvinyl pyrrolidone, gelatine, sugars, starches and other pharmaceutically acceptable substances with cohesive properties. Suitable surfactants are found in the groups of pharmaceutically acceptable non-ionic surfactants, such as polysorbate 80, or ionic surfactants such as for instance sodium lauryl sulfate.

Optionally an osmotic agent is placed in the core material. Such an osmotic agent is water soluble and will provide an osmotic pressure in the tablet. Examples of osmotic agents are magnesium sulfate, sodium chloride, lithium chloride, potassium chloride, potassium sulfate, sodium carbonate, lithium sulfate, calcium bicarbonate, sodium sulfate, calcium lactate, urea, magnesium succinate, sucrose or mixtures thereof.

Alternatively, the active substance optionally mixed with any of the components defined above can be formulated into a core material. Said core material may be produced by extrusion/spheronization, balling or compression utilizing different process equipments. For extrusion/spheronization processes incorporation of a microcrystalline cellulose and a low-substituted hydroxypropylcellulose in the core material is preferred. The size of the formulated core materials is approximately between 0.1 and 4 mm, preferably between 0.1 and 2 mm for a pellet preparation, and between 2 and 10 mm, preferably between 3 and 7 mm for a tablet preparation.

Suitable alkaline additives can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16} CO_3.4H_2O)$, $MgO.Al_2O_3.2SiO_2.nH_2O$ or similar compounds; organic pH-buffering substances such as trihydroxymethylaminomethane, basic amino acids such as arginine, and their salts or other similar, pharmaceutically acceptable pH-buffering substances.

Alternatively, the aforementioned core material for a pellet preparation can be prepared by using spray drying or congealing techniques.

Swelling Layer

The applied swelling layer comprises one or more water swellable substances, a suitable binder, and optionally pharmaceutically acceptable excipient(s). Suitable swellable substances, binders, as well as pharmaceutically acceptable excipients are described below. The swelling layer expands when exposed for an aqueous solution such as intestinal fluid.

Alternatively, one of the additional drug containing layers applied onto the core material may be a combined drug swelling layer.

Water Swellable Substances

Water swellable substances suitable for the dosage forms according to the present invention are compounds which are able to expand when they are exposed to an aqueous solution, such as intestinal fluid.

One or more water swellable substances may be present in the core material together with the active substance and optionally pharmaceutically acceptable excipient(s). Alternatively, one or more water swellable substances are included in a swelling layer applied onto the core material. As a further alternative, swellable substances(s) they may also be present in an optional swelling layer situated beneath the drug containing layer, if a layered seed or sphere is used as the core material.

The amount and art of water swellable substance(s) in the swelling layer or in the core to material is chosen in such a way that the core material or the swelling layer in contact with an aqueous solution, such as intestinal fluid, will expand to such a degree that the surrounding lag-time controlling membrane ruptures. A water swellable substance may also be included in the drug comprising layer of the multiple layered pellets or tablets to increase dissolution rate of the drug fraction.

Suitable substances which can be used as water swellable substances are for instance, low-substituted hydroxypropyl cellulose, e.g. L-HPC; cross-linked polyvinyl pyrrolidone (PVP-XL), e.g. Kollidon™ CL and Polyplasdone™ XL; cross-linked sodium carboxymethylcellulose, e.g. Ac-di-sol™, Primellose™; sodium starch glycolate, e.g. Primojel™; sodium carboxymethylcellulose, e.g. Nymcel ZSB10™; sodium carboxymethyl starch, e.g. Explotab™; ion-exchange resins, e.g. Dowex™ or Amberlite™; microcrystalline cellulose, e.g. Avicel™; starches and pregelatinized starch, e.g. Starch 1500™, Sepistab ST200 ™; and formalin-casein, e.g. Plas-Vita™. One of these substances can be used or any combinations or mixtures thereof, taking into consideration that the use of any acidic compound not is suitable.

Lag Time Controlling Layer

The lag time controlling layer is a semipermeable membrane comprising a water resistant polymer that is semipermeable for an aqueous solution, such as intestinal fluid. Suitable polymers are cellulose acetate, ethylcellulose, polyvinyl acetate, cellulose acetate butyrate, cellulose acetate propionate, acrylic acid copolymers, such as Eudragit™ RS or RL. The polymer may optionally comprise pore forming agents, such as a water soluble substance, e.g. sucrose, salt; or a water soluble polymer eg. polyethylene glycol. Also pharmaceutically acceptable excipients such as fillers and membrane strength influencing agents such as talc, aerosil, or sodium aluminium silicate may be included.

There is at least one lag time controlling layer present in the dosage forms according to the invention. The lag time controlling layer positioned nearest the inner core material is constructed in the form of a semipermeable membrane that will disrupt after a desired time after ingestion.

A desired lag time may be adjusted by the composition and thickness of the layer. The amount of substances forming such a disrupting semipermeable membrane, i.e. a lag time controlling layer, is usually in the range from 0.5 to 25 % counted on the weight of the core material including swelling substances or a swelling layer. Preferably the amount of such a lag time controlling layer, i.e. a disrupting semipermeable membrane, is between 2 to 20% by weight.

A preferred disrupting semipermeable membrane, i.e. lag time controlling layer, is composed of a mixture of ethylcellulose and talc. The mixture contains most preferably 10 to 80% w/w of talc.

Optionally, any additional lag time controlling layer may be constructed as a disrupting semipermeable membrane.

Enteric Coating Layer(s) and Separating Layer(s)

Before applying an enteric coating layer onto the layered pellets or tablets, they may optionally be covered with one or more separating layers comprising pharmaceutical excipients optionally including alkaline compounds such as for instance pH-buffering compounds. This separating layer separates the composition of the layered pellets or tablets from the outer enteric coating layer.

The separating layer as well as the other type of layers, such as the swelling and lag time controlling layers, can be applied by coating or layering procedures in suitable equipment such as a coating pan, coating granulator, or centrifugal granulator or in a fluidized bed apparatus (including Wurster type) using water and/or organic solvents for the coating process. As an alternative the layer(s) can be applied by using powder coating or press-coating techniques.

Suitable materials for the optional separating layer are pharmaceutically acceptable compounds such as, for instance, sugar, polyethylene glycol, polyvinyl pyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc, pH-buffering substances and other additives may also be included into the separating layer.

When the optional separating layer is applied to the layered pellets or tablets it may constitute a variable thickness. The maximum thickness of the optional separating layer is normally only limited by processing conditions. The separating layer may serve as a diffusion barrier and may act as a pH-buffering zone. The optional separating layer may improve the chemical stability of the active substance and/or the physical properties of the dosage form.

Finally the layered pellets or tablets are covered by one or more enteric coating layers by using a suitable coating technique. The enteric coating layer material may be dispersed or dissolved in either water or in suitable organic solvents. As enteric coating layer polymers one or more, separately or in combination, of the following can be used; e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethyl ethylcellulose, shellac or other suitable enteric coating layer polymer(s).

Additives such as dispersants, colorants, pigments, additional polymers e.g. poly(ethylacrylate, methylmethacrylate), anti-tacking and anti-foaming agents may also be included into the enteric coating layer. Other compounds may be added to increase film thickness and to decrease diffusion of acidic gastric juices into the acid susceptible material. The enteric coating layer(s) constitutes a thickness of approximately at least 10 μm, preferably more than 20 μm. The maximum thickness of the applied enteric coating layer(s) is normally only limited by processing conditions.

Any of the applied polymer containing layers, and specially the enteric coating layers may also contain pharmaceutically acceptable plasticizers to obtain desired mechanical properties. Such plasticizers are for instance, but not restricted to, triacetin, citric acid esters, phthalic acid esters, dibutyl sebacate, cetyl alcohol, polyethylene glycols, glycerol monoesters, polysorbates or other plasticizers. The amount of plasticizer is preferably optimized for each formula, in relation to the selected polymer(s), selected plasticizer(s) and the applied amount of said polymer(s).

Final Dosage Form

The prepared layered pellets, optionally mixed with tablet excipients are filled into a capsule, or compressed into a multiple unit tableted dosage form. Alternatively, the dosage form is a multiple layered tablet. Prepared tablets are optionally covered with filmforming agent(s) to obtain a smooth surface of the tablet and further enhance the stability of the tablet during packaging and transport. Such a tablet coating layer may further comprise additives like anti-tacking agents, colorants and pigments or other additives to obtain a tablet of good appearance.

The dosage forms according to the invention are suitable for oral administration. The dose will depend on the nature and severity of the disease to be treated The dose may also vary according to the age, body weight, and response of the individual patient. Children and patients with liver diseases as well as patients under long term treatment will generally benefit from doses that are somewhat lower than the average. In the treatment of other conditions higher doses than average will be used.

Preferably, a dosage form of the proton pump inhibitor, for instance 1–500 mg is administered once a day. Suitable doses comprise for instance about 5–100 mg of the substance, and more preferably 10–80 mg. The dosage form may be administered together with other suitable drugs, such as antibacterial compound(s), NSAID(s), motility stimulating agents, and/or antacids.

EXAMPLES

The following examples describe the invention more in detail without restricting it.

Example 1

Pulsed single dose delayed release layered pellets comprising magnesium salt of S-omeprazole (pellet strength approx. 44 mg/g).

Preparation of Core Material (Spheres Layered with Drug)

A drug containing suspension was made according to the composition below;

| | |
|---|---|
| S-omeprazole Mg-salt | 100 g |
| HPMC, 6 cps | 15 g |
| Polysorbate 80 | 2 g |
| Purified water | 323 g |

HPMC was dissolved in water during stirring with subsequent addition of Polysorblite 80 and the drug. The suspension was sprayed onto 290 g of sugar spheres (Nonpareil) in a fluidized bed. The weight of the obtained product was 395 g.

Application of a Swelling Layer

A (water free) suspension containing in water swellable substances was prepared according to the following composition;

| | |
|---|---|
| Low-substituted hydroxypropylcellulose (L-HPC) | 162 g |
| Hydroxypropylcellulose LF (HPC-LF) | 74 g |
| Talc | 354 g |
| EtOH (99.5%) | 3100 g |

HPC-LF was dissolved in ethanol during stirring, then talc and swelling agent L-HPC was added. The suspension was sprayed onto 175 g of the core material from above in a Wurster equipped fluidized bed. The weight of the obtained product was 711 g.

Application of Lag Time Controlling Layer (Semipermeable Membrane)

A coating suspension was made according to the following formula;

| | |
|---|---|
| Ethylcellulose, 10 cps | 10 g |
| Talc | 23 g |
| EtOH (99.5%) | 1000 g |

The ethylcellulose was dissolved in the ethanol during stirring, then talc was added. Spraying of the suspension onto 150 g of swelling layered pellets from above (0.61–0.71 mm obtained by sieving) was done in a Wurster equipped fluidized bed. The weight of the obtained pellets was 176 g.

Pellets (corresponding to approx. 10 mg active substance) were analyzed using USP dissolution apparatus No. 2 (paddle), and operated at 100 rpm, 37° C. and with a phosphate buffer pH 6.8. The dissolution of active substance was followed by registration of the absorbance at 292 nm in a buffer solution, using a 0.5 cm flow-through compact cell. The dissolution profile measured at 292 nm is shown in FIG. 1.

Example 2

Pulsed single dose delayed release layered pellets comprising magnesium salt of S-omeprazole (pellet strength approx. 43 mg/g).

Preparation of Core Material (Spheres Layered with Drug)

A drug containing suspension was made according to the composition below;

| | |
|---|---|
| S-omeprazole Mg-salt | 100 g |
| HPMC, 6 cps | 15 g |
| Polysorbate 80 | 2 g |
| Purified water | 323 g |

HPMC was dissolved in water during stirring with subsequent addition of Polysorbate 80 and the substance. The suspension was sprayed onto 290 g of sugar spheres (Nonpareil) in a fluidized bed. After coating the weight of the obtained product was 395 g.

Application of Swelling Layer

A water free suspension containing in water swellable substances was prepared according to the following composition;

| | |
|---|---|
| Low-substituted hydroxypropylcellulose (L-HPC) | 162 g |
| Hydroxypropylcellulose LF (HPC-LF) | 74 g |
| Talc | 354 g |
| EtOH (99.5%) | 3100 g |

HPC-LF was dissolved in ethanol during stirring, then talc and swelling agent L-HPC was added. The suspension was sprayed onto 175 g pellets from above in a Wurster equipped fluidized bed. The weight of the obtained product was 711 g.

Application of Lag Time Controlling Layer (Semipermeable Membrane)

100 g of the swelling layered pellets obtained above were coated to obtain a lag-time controlling layer with the suspension below;

| | |
|---|---|
| Ethylcellulose, 10 cps | 8 g |
| Talc | 9 g |
| Mg-Stearate | 2 g |
| EtOH (99.5%) | 620 g |

The suspension was prepared by dissolving the ethylcellulose in the ethanol during stirring, then the other compounds were added. Spraying of the suspension onto the pellets was done in a Wurster equipped fluidized bed. The weight of the obtained pellets was 116 g.

The pellets were analyzed as is described in Example 1. The dissolution profile is shown in FIG. 2.

Example 3

Single dose layered pellets, i.e. enteric coated pulsed single dose delayed release pellets comprising magnesium salt of S-omeprazole (pellet strength approx. 37 mg/g).

Application of Enteric Coating Layer

Pellets from Example I were enteric coated in a fluidized bed with a coating dispersion according to below;

| | |
|---|---|
| Eudragit L30 D-55 (30% w/w dispersion) | 73.3 g |
| Triethylcitrate (TEC) | 6.6 g |
| Glycerole monostearate (GMS) | 0.3 g |
| Polysorbate 80 | 0.03 g |
| Purified water | 40.4 g |

A homogenous coating dispersion was prepared by dispersing polysorbate 80 and glycerol monostearate in water. Triethylcitrate was dissolved in the Eudragit dispersion and thereafter the two dispersions were mixed to obtain the coating dispersion.

The coating dispersion was applied onto 120 g pellets from Example 1, using a Wurster equipped fluidized bed. The weight of the layered pellets was 140 g.

Pellets (corresponding to approx. 10 mg active substance) were analyzed using USP dissolution apparatus No. 2 (paddle) and operated at 100 rpm and 37° C. First the pellets were immersed n 0.1M HCl for 2 hours (pH 1.2), thereafter phosphate buffer components were added to obtain pH 6.8. The dissolution profile was registered as described in example 1, and is shown in FIG. 3. The pellets were examined with respect to acid resistance. After exposure to 0.1 M HCl during two hours, 96% of the active substance remained intact.

Example 4

Single dose layered pellets, i.e. enteric coated pulsed single dose delayed release pellets comprising magnesium salt of omeprazole (pellet strength approx. 35 mg/g.).

Preparation of Core Material (Spheres Layered with Drug)

A drug containing suspension was made according to the composition below;

| | |
|---|---|
| Omeprazole Mg-salt | 100 g |
| HPMC, 6 cps | 15 g |
| Polysorbate 80 | 2 g |
| Purified water | 323 g |

HPMC was dissolved in the water during stirring with subsequent addition of Polysorbate 80 and the drug. The suspension was sprayed onto 290 g of sugar spheres (Nonpareil) in a fluidized bed. After the coating the weight of the obtained product was 395 g.

Application of Swelling Layer

A (water free) suspension containing in water swellable substances was prepared according to the following composition;

| | |
|---|---|
| Low-substituted hydroxypropylcellulose (L-HPC) | 162 g |
| Hydroxypropylcellulose LF (HPC-LF) | 74 g |
| Talc | 354 g |
| EtOH (99.5%) | 3100 g |

HPC-LF was dissolved in ethanol during stirring, then the talc and the swelling agent L-HPC was added. The suspension was sprayed onto 175 g of core material from above in a Wurster equipped fluidized bed. The weight of the obtained product was 711 g.

Application of Lag Time Controlling Layer (Semipermeable Membrane)

120 grams of the swelling layered pellets (the fraction 0.61 mm–0.71 mm obtained by sieving) obtained above were coated with the suspension below;

| | |
|---|---|
| Ethylcellulose, 10 cps | 8 g |
| Talc | 18 g |
| EtOH (99.5%) | 810 g |

The suspension was prepared by dissolving ethylcellulose in ethanol during stirring, then talc was added. The suspension was sprayed onto the pellets in a Wurster equipped fluidized bed. The weight of the obtained product was 137 g.

Application of Enteric Coating Layer 120 grams of the pellets from the previous step above were coated with an enteric coating solution according to below;

| | |
|---|---|
| HPMCP (HP-55) | 33 g |
| Cetanol | 2.4 g |
| Acetone | 353 g |
| EtOH (99.5%) | 151 g |

The coating solution was prepared by dissolving HPMCP and cetanol in a mixture of the solvents during stirring. The coating solution was applied in a Wurster equipped fluidized bed. The weight of the layered pellets was 149 g.

The layered pellets were examined with respect to acid resistance in 0.1 M HCl. The acid resistance was 97%.

Example 5

Single dose layered tablets, i.e. enteric coated pulsed single dose delayed release tablets comprising magnesium salt of S-omeprazole (Tablet strength approx. 16 mg).

Granules

Granules for homogenous tablet cores were made according to the following composition;

| | |
|---|---|
| S-omeprazole Mg-salt | 229 g |
| Microcrystalline cellulose, Avicel pH 101 | 151 g |
| Microcrystalline cellulose, Avicel PH 102 sp. coarse grade | 400 g |
| L-HPC | 256 g |
| PVP-XL | 302 g |
| Sodium laurylsulphate (SLS) | 30 g |
| Water purified | 1060 g |

A granulating solution was prepared by dissolving the SLS in 460 g of purified water.

The powders above were mixed in a mixer after which the solution was added in an even stream. Thereafter approx. 600 g water was added during continued mixing, to give satisfactory consistency to the mass.

The mass was dried in a drying oven at 50° C. over night.

Preparation of Tablet Cores

After milling through a 1.0 mm screen the obtained granules were mixed with tablet lubricant, sodium chloride, and an additional amount of swellable substance, according to the following composition;

| | |
|---|---|
| Granules for tablet core | 400 g |
| Sodium chloride (passing 0.3 mm) | 80 g |
| Sodium stearyl fumarate (Pruv ®) | 8 g |
| Polyvinyl pyrrolidone cross-linked (PVP-XL) | 20 g |

The mixing was performed to homogeneity in a Kenwood mixer.

The mixture was compressed to 6 mm in diameter tablets having an average weight of 126 mg, on a single punch tableting machine (Diaf).

Application of Lag Time Controlling Layer (Semipermeable Membrane)

The tablets from previous step were coated in a Wurster equipped fluidized bed coating apparatus with a coating suspension of the following composition;

| | |
|---|---|
| EtOH 99.5% (w/v) | 291 parts by weight |
| Ethyl cellulose N-10 | 11 parts by weight |
| Talc, micronized | 7 parts by weight |
| Sum: | 309 parts. |

200 grams of tablets were processed and the coating was continued until the average tablet weight was 134 mg.

Application of Enteric Coating Layer

The tablets obtained in the previous step were coated with an enteric coating layer in the same equipment as for the preceding coating step. The coating solution had the following composition;

| | |
|---|---|
| Hydroxypropyl methylcellulose phtalate (HP-55 ®) | 16 parts by weight |
| Cetanol | 1 parts by weight |
| Acetone | 151 parts by weight |
| Ethanol (95% w/v) | 65 parts by weight |
| Sum: | 233 parts |

100 grams of the tablets were processed and the coating was continued until the average tablet weight was 148 mg.

Individual tablets were analyzed using USP dissolution apparatus No. 2 (paddle) equipped with stationary baskets and operated at 100 rpm and 37° C. First the tablets were pre-exposed for 0.1 M HCl for two hours (pH 1.2), whereafter the dissolution medium was changed to phosphate buffer pH 6.8.

The dissolution profile obtained was registered as described in example 1, and can be seen in FIG. 4.

Example 6

Multiple dose layered tablets, i.e. enteric coated dual pulsed multiple release tablets. (tablet strength approx. 2×15 mg).

Granules

Granules for tablet cores were made according to the following composition;

| | |
|---|---|
| S-omeprazole Mg-salt | 229 g |
| Microcrystalline cellulose, Avicel PH 101 | 151 g |
| Microcrystalline cellulose, Avicel PH 102 sp. Coarse grade | 400 g |
| L-HPC | 256 g |
| PVP-XL | 302 g |
| Sodium laurylsulphate (SLS) | 30 g |
| Water purified | 1060 g |

A granulating solution was prepared by dissolving the SLS in 460 g of purified water. The powders above were mixed in a mixer after which the solution was added in an even stream. Thereafter approx. 600 g water was added during continued mixing, to give satisfactory consistency to the mass.

The mass was dried in a drying oven at 50° C. over night.

Preparation of Tablet Cores

After milling through a 1.0 mm screen the obtained granules were mixed with tablet lubricant, sodium chloride, .and an additional amount of swellable substance, according to the following composition;

| | |
|---|---|
| Granules for homogenous tablet core | 400 |
| Sodium chloride (passing 0.3 mm) | 80 |
| Sodium stearyl fumarate (Pruv ®) | 8 |
| Polyvinyl pyrrolidone cross-linked (PVP-XL) | 20 |

The mixing was performed to homogeneity in a Kenwood mixer.

The mixture was compressed to 6 mm in diameter tablets having an average weight of 126 mg, on a single punch tableting machine (Diaf).

Application of Lag Time Controlling Layer (Semipermeable Membrane)

The tablets from previous step were coated in a Wurster equipped fluidized bed coating apparatus with a coating suspension of the following composition;

| | |
|---|---|
| EtOH 99.5% (w/v) | 291 parts by weight |
| Ethyl cellulose N-10 | 11 parts by weight |
| Talc, micronized | 7 parts by weight |
| Sum: | 309 parts. |

200 grams of tablets were processed and the coating was continued until average tablet weight was 134 mg.

Application of a Drug Comprising Layer

The tablets obtained in previous step were coated in the same equipment as above with a coating suspension of the following composition;

| | |
|---|---|
| S-omeprazole Mg-salt | 20 parts by weight |
| Hydroxypropyl methylcellulose 6 cps | 13 parts by weight |
| Ethanol 99% | 128 parts by weight |
| Water purified | 128 parts by weight |
| Sum: | 289 parts. |

99 grams of tablets were processed and the coating was continued until the average tablet weight was 162 mg.

Application of Enteric Coating Layer

The tablets obtained in previous step were coated with an enteric coating layer in the same equipment as for the preceding coating step. The coating solution had the following composition;

| | |
|---|---|
| Hydroxypropyl methylcellulose phtalate (HP-55) | 16 parts by weight |
| Cetanol | 1 parts by weight |
| Acetone | 153 parts by weight |
| Ethanol (95% w/v) | 65 parts by weight |
| Sum: | 235 parts |

119 grams of the tablets were processed and the coating was continued until the average tablet weight was 173 mg.

Individual tablets were analyzed using USP dissolution apparatus No. 2 (paddle) equipped with stationary baskets and operated at 100 rpm and 37° C. First the tablets were pre-exposed for 0.1 M HCl for two hours, whereafter the dissolution medium was changed to phosphate buffer pH 6.8.

The dissolution profile obtained was registered as described in example 1, and can be seen in FIG. 5. The acid resistance of the tablets were examined and the result was 98%.

Example 7

Multiple dose capsule formulation comprising (2×20) mg of omeprazole in the form of enteric coated pellets, mixed with an enteric coated tablet with delayed release.

| | |
|---|---|
| Suspension layering | |
| Magnesium omeprazole | 5 kg |
| Sugar spheres cores (0.25–0.355 mm diam.) | 10 kg |
| Hydroxypropyl methylcellulose | 0.8 kg |
| Water purified | 20 kg |
| Separating layer | |
| Drug containing cores (acc. to above) | 14.6 kg |
| Hydroxypropyl cellulose | 1.5 kg |
| Talc | 2.5 kg |
| Magnesium Stearate | 0.2 kg |
| Water purified | 29 kg |
| Enteric coating | |
| Pellets (acc. to above) | 9 kg |
| Methacrylic acid copolymer (30% suspension) | 15 kg |
| Triethyl citrate | 1.4 kg |
| Mono- and diglycerides (NF) | 0.2 kg |
| Polysorbate 80 | 0.02 kg |
| Water purified | 9 kg |
| Over-coating | |
| Enteric coated pellets | 9 kg |
| Hydroxypropyl methylcellulose | 0.2 kg |

| | |
|---|---|
| Mg-Stearate | 0.005 kg |
| Water purified | 3.6 kg |

Suspension layering was performed in a fluid bed apparatus. Magnesium omeprazole was sprayed onto inert sugar sphere cores from a water suspension containing the dissolved binder.

The prepared core material was sub-coated in a fluid bed apparatus with a hydroxypropyl cellulose solution containing talc and magnesium stearate. The enteric coating consisting of methacrylic acid copolymer, mono- and diglycerides, triethylcitrate and polysorbate was sprayed onto the sub-coated pellets in a fluid bed apparatus. In the same type of apparatus the enteric coated pellets were coated with hydroxypropyl methylcellulose/Mg-Stearate suspension. The over-coated pellets were classified by sieving, to pass 0.71 mm.

The product was analyzed and found to contain 209 mg/g Mg-omeprazole.

Single dose layered tablets, i.e. enteric coated delayed release tablets comprising magnesium salt of omeprazole. (Tablet strength approx. 16 mg.)

Granules

Granules for tablet cores were made according to the following composition (parts by weight);

| | |
|---|---|
| Omeprazole Mg-salt | 229 g |
| Microcrystalline cellulose, Avicel PH 101 | 145 g |
| Microcrystalline cellulose, Avicel PH 102 sp. coarse grade | 400 g |
| L-HPC | 251 g |
| PVP-XL | 302 g |
| Hydroxy methylcellulose 6 cps | 11 g |
| Sodium laurylsulphate (SLS) | 30 g |
| Water purified | 960 g |

A granulating solution was prepared by dissolving the SLS in 460 g of purified water.

The powders above were mixed in a mixer after which the solution was added in an even stream. Thereafter approx. 500 g water was added during continued mixing, to give satisfactory consistency to the mass.

The mass was dried in a drying oven at 50° C. over night.

Preparation of Tablet Cores

After milling through a 1.0 mm screen the obtained granules were mixed with tablet lubricant, sodium chloride and an additional amount of swellable substance, according to the following composition;

| | |
|---|---|
| Granules for tablet core | 400 g |
| Sodium chloride (passing 0.3 mm) | 80 g |
| Sodium stearyl fumarate (Pruv ®) | 8 g |
| Polyvinyl pyrrolidone cross-linked (PVP-XL) | 20 g |

The mixing was performed to homogeneity in a Kenwood mixer.

The mixture was compressed to 6 mm in diameter tablets having an average weight of 126 mg, on a single punch tableting machine (Diaf).

Application of Lag Time Regulating Layer (Semipermeable Membrane)

The tablets from previous step were coated in a Wurster equipped fluidized bed coating apparatus with a coating suspension of the following composition;

| | |
|---|---|
| EtOH 99.5% (w/v) | 291 parts by weight |
| Ethyl cellulose N-10 | 11 parts by weight |
| Talc, micronized | 7 parts by weight |
| Sum: | 309 parts. |

200 grams of tablets were processed and the coating was continued until the average tablet weight was 134 mg.

Application of Enteric Coating Layer

The tablets obtained in previous step were coated with an enteric coating layer in the same equipment as for the preceding coating step. The coating solution had the following composition;

| | |
|---|---|
| Hydroxypropyl methylcellulose phtalate (HP-55 ®) | 16 parts by weight |
| Cetanol | 1 parts by weight |
| Acetone | 151 parts by weight |
| Ethanol (95% w/v) | 65 parts by weight |
| Sum: | 233 parts |

100 grams of the tablets were processed and the coating was continued until the average tablet weight was 148 mg.

Filling of Capsule 0.10 g of the pellets prepared above and one of the layered tablets obtained above were filled in a hard gelatine capsule size 1.

The best mode to practice the invention is according to the description given in Example 6.

What is claimed is:

1. An enteric coated pharmaceutical dosage form comprising an H$^+$,K$^+$-ATPase inhibitor, a distruptable semi-permeable membrane and one or more swellable substances, wherein the dosage form has an instant inhibitor-releasing part and at least one delayed inhibitor-releasing part, and is capable of giving a discontinuous release of the H$^+$,K$^+$-ATPase inhibitor in the form of at least two consecutive pulses separated in time from 0.5 up to 12 hours, and the H$^+$,K$^+$-ATPase inhibitor is a compound of the formula I

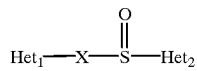

wherein

Het$_1$ is

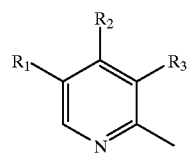 or 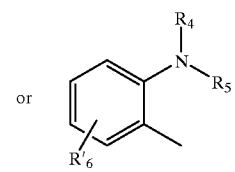

Het₂ is

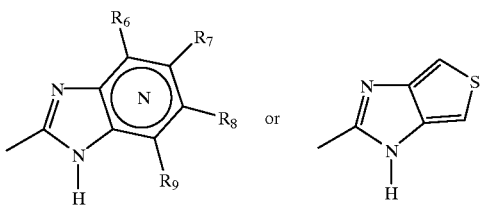

X=

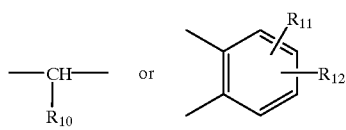

wherein
- N in the benzimidazole moiety means that one of the ring carbon atoms substituted by $R_6$–$R_9$ optionally may be exchanged for a nitrogen atom without any substituents;
- $R_1$, $R_2$ and $R_3$ are the same or different and selected from the group consisting of hydrogen, alkyl, alkoxy, fluorine-substituted alkoxy, alkylthio, alkoxyalkoxy, dialkylamino, piperidino, morpholino, halogen, phenyl and phenylalkoxy;
- $R_4$ and $R_5$ are the same or different and selected from the group consisting of hydrogen, alkyl and arylalkyl;
- $R_6'$ is selected from the group consisting of hydrogen, halogen, trifluoromethyl, alkyl and alkoxy,
- $R_6$–$R_9$ are the same or different and selected from the group consisting of hydrogen, alkyl, alkoxy, halogen, haloalkoxy, alkylcarbonyl, alkoxycarbonyl, oxazolinyl, and trifluoroalkyl, or adjacent groups $R_6$–$R_9$ form ring structures;
- $R_{10}$ is hydrogen or forms an alkylene chain together with $R_3$; and
- $R_{11}$ and $R_{12}$ are the same or different and selected from the group consisting of hydrogen, halogen and alkyl.

2. The dosage form according to claim 1, wherein the $H^+,K^+$-ATPase inhibitor is omeprazole, an alkaline salt of omeprazole, the (−)-enantiomer of omeprazole or an alkaline salt of the (−)-enantiomer of omeprazole.

3. The dosage form according to claim 2, wherein the alkaline salt is a magnesium salt.

4. The dosage form according to claim 1, wherein the $H^+,K^+$-ATPase inhibitor is lansoprazole, an alkaline salt of lansoprazole, a single enantiomer of lansoprazole, or an alkaline salt of the single enantiomer.

5. The dosage form according to claim 1, wherein the inhibitor-releasing parts makeup a unit comprising (a) the core material which comprises a portion of the $H^+,K^+$-ATPase inhibitor, the water swellable substance, and optionally pharmaceutically acceptable excipients, and (b) the following sequence of layers covering the core material:
 1) a lag time controlling layer,
 1) at least one additional layer comprising another portion of the $H^+,K^+$-ATPase inhibitor, and
 3) an enteric coating layer.

6. The dosage form according to claim 1, wherein the inhibitor-releasing parts makeup a unit comprised of (a) a core material which comprises a portion of the $H^+,K^+$-ATPase inhibitor and optionally pharmaceutically acceptable excipients, and (b) the following sequence of layers covering the core material:
 1) a swelling layer comprising a water swellable substance,
 2) a lag time controlling layer,
 3) at least one additional layer comprising another portion of the $H^+,K^+$-ATPase inhibitor, and
 4) an enteric coating layer.

7. The dosage form according to claim 1, wherein the inhibitor-releasing parts are in the form of units selected from the group consisting of pellets, tablets and combinations thereof.

8. The dosage form according to claim 7, wherein the content of the inhibitor-releasing parts comprises the following:
 (a) a first inhibitor-releasing part comprising a respectively associated first core material which comprises a portion of the $H^+,K^+$-ATPase inhibitor, a water swellable substance, and optionally pharmaceutically acceptable excipients, wherein the first core material is covered, in sequence, by a lag time controlling layer which is the disruptable semi-permeable membrane and a respectively associated first enteric coating layer, and
 (b) a second inhibitor-releasing part comprising a respectively associated second core material which comprises another portion of $H^+,K^+$-ATPase inhibitor and optionally pharmaceutically acceptable excipients, wherein the second core material is covered by a respectively associated second enteric coating layer.

9. The dosage form according to claim 7, wherein the content of the inhibitor-releasing parts comprise the following:
 (a) a first inhibitor-releasing part comprising a respectively associated first core material which comprises a portion of the $H^+,K^+$-ATPase inhibitor and optionally pharmaceutically acceptable excipients, wherein the first core material is covered, in sequence, by a swelling layer comprising a water swellable substance, a lag time controlling layer which is the disruptable semi-permeable membrane and a respectively associated first enteric coating layer, and
 (b) a second inhibitor-releasing part comprising a respectively associated second core material which comprises another portion of the $H^+,K^+$-ATPase inhibitor and optionally pharmaceutically acceptable excipients, wherein the second core material is covered by a respectively associated second enteric coating layer.

10. The dosage form according to claim 1, wherein the consecutive pulses are separated in time from 0.5 up to 4 hours.

11. The dosage form according to any one of claims 5–7, 8 or 9, wherein the $H^+,K^+$-ATPase inhibitor is in admixture with an alkaline additive.

12. The dosage form according to any one of claims 5, 6, 8 or 9, wherein the water swellable substance is selected from the group consisting of low-substituted hydroxypropyl cellulose, cross-linked polyvinyl pyrrolidone, cross-linked sodium carboxymethyl cellulose and sodium starch glycolate.

13. The dosage form according to any one of claims 5, 6, 8, or 9, wherein the disruptable semi-permeable membrane consists essentially of one or more water resistant polymers and pharmaceutically acceptable excipients.

14. The dosage form according to claim 13, wherein the water resistant polymer is selected from the group consisting of cellulose acetate, ethyl cellulose, polyvinyl acetate, cellulose acetate butyrate, cellulose acetate propionate and acrylic acid copolymers.

15. The dosage form according to any one of claims 5, 6, 8 or 9, wherein the weight of the lag time controlling layer constitutes from 0.5 to 25% based on the combined weight of the core material and the water swellable substance or the swelling layer.

16. The dosage form according to claim 8 or 9, wherein the inhibitor-releasing parts are filled in a capsule.

17. The dosage form according to claim 8 or 9, wherein the inhibitor-releasing parts are mixed together with pharmaceutically acceptable excipients and compressed into a multiple unit tableted dosage form.

18. The dosage form according to claim 5 or 6, wherein a separating layer is present beneath the enteric coating layer.

19. The dosage form according to claim 5 or 6, wherein the core material further comprises a seed layered with the $H^+,K^+$-ATPase inhibitor.

20. A layered pellet or tablet comprising the dosage form according to claim 5 or 6.

21. The dosage form according to claim 8 or 9, wherein one or more additional layers comprising an additional portion of the $H^+,K^+$-ATPase inhibitor is applied under the enteric coating layer of the first inhibitor-releasing part (a).

22. A process for the preparation of an enteric coated pharmaceutical dosage form comprising an $H^+,K^+$-ATPase inhibitor and having an instant inhibitor-releasing part and at least one delayed inhibitor-releasing part, wherein the dosage form is capable of giving a discontinuous release of the $H^+,K^+$-ATPase inhibitor in the form of at least two separate pulses, and wherein the process comprises the following steps:
   (a) mixing a portion of the $H^+,K^+$-ATPase inhibitor, a water swellable substance, and optionally pharmaceutically acceptable excipients to obtain a core material, and
   (b) applying in sequence, the following layers onto the core material to obtain the dosage form:
      1) a lag time controlling layer which is the disruptable semi-permeable membrane,
      2) a layer comprising another portion of the $H^+,K^+$-ATPase inhibitor, and
      3) an enteric coating layer.

23. A process for the preparation of an enteric coated pharmaceutical dosage form comprising an $H^+,K^+$-ATPase inhibitor and having an instant inhibitor-releasing part and at least one delayed inhibitor-releasing part, wherein the dosage form is capable of giving a discontinuous release of the $H^+,K^+$-ATPase inhibitor in the form of at least two separate pulses, and wherein the process comprises the following steps:
   (a) shaping a portion of the $H^+,K^+$-ATPase inhibitor optionally mixed with pharmaceutically acceptable excipients to obtain a core material, and,
   (b) applying, in sequence, the following layers onto the core material to obtain the dosage form:
      1) a swelling layer comprising a water swellable substance,
      2) a lag time controlling layer which is the disruptable semi-permeable membrane,
      3) a layer comprising another portion of the $H^+,K^+$-ATPase inhibitor, and
      4) an enteric coating layer.

24. A process for the preparation of a dosage form according to claim 22 or 23, wherein an additional layer comprising another portion of the $H^+,K^+$-ATPase inhibitor is applied before the enteric coating layer is applied.

25. A method for improving inhibition of gastric acid secretion which comprises administering to a patient in need thereof, an oral pharmaceutical dosage form as defined in any one of claims 1–7, 8 or 9.

26. A method for improving the therapeutic effect in the treatment of gastrointestinal disorders associated with excess acid secretion which comprises administering to a patient in need thereof, an oral pharmaceutical dosage form as defined in any one of claims 1–7, 8 or 9.

27. The dosage form according to claim 1, wherein the $H^+,K^+$-ATPase inhibitor is an alkaline salt, a single enantiomer or an alkaline salt of the single enantiomer of the compound of formula I.

28. The dosage form according to claim 8 or 9, wherein a separating layer is present beneath at least one of the enteric coating layers.

29. The dosage form according to claim 8 or 9, wherein at least one of the core materials further comprises a seed layered with the $H^+,K^+$-ATPase inhibitor.

30. The layered pellet or tablet according to claim 20, wherein at least one additional layer comprising another portion of the $H^+,K^+$-ATPase inhibitor is applied under the enteric coating.

31. The dosage form according to claim 1, wherein the at least consecutive pulses are separated in time from 0.5 up to 8 hours.

32. The dosage form according to claim 14, wherein the pharmaceutically acceptable excipient is selected from the group consisting of talc, aerosil and sodium aluminum silicate.

33. The dosage form according to claim 32, wherein the semi-permeable membrane consists essentially of ethyl cellulose and talc.

34. The process according to claim 22 or 23, wherein the disruptable semi-permeable membrane consists essentially of one or more water resistant polymers and pharmaceutically acceptable excipients.

35. The process according to claim 34, wherein the water resistant polymer is selected from the group consisting of cellulose acetate, ethyl cellulose, polyvinyl acetate, cellulose acetate butyrate, cellulose, acetate propionate and acrylic acid copolymers.

36. The process according to claim 35, wherein the pharmaceutically acceptable excipient is selected from the group consisting of talc, aerosil and sodium aluminum silicate.

37. The process according to claim 36, wherein the semi-permeable membrane consists essentially of ethyl cellulose and talc.

* * * * *

UNITED STATES PATENT AND TRADEMARK OFFICE
CERTIFICATE OF CORRECTION

PATENT NO. : 6,610,323 B1
DATED : August 26, 2003
INVENTOR(S) : Lundberg et al.

It is certified that error appears in the above-identified patent and that said Letters Patent is hereby corrected as shown below:

<u>Title page,</u>
Item [86], §371 date, delete "June 2, 2000" and substitute therefor -- Jan. 15, 1999 --.

<u>Column 1,</u>
Lines 5-6, delete "Dec. 18, 1998" and substitute therefor -- Dec. 17, 1998 --.

<u>Column 7, line 62 and Column 8, line 20,</u>
Delete ";" (two occurrences) and substitute therefor -- : --.

<u>Column 10,</u>
Line 39, delete "eg." and substitute therefore -- e.g. --.

<u>Column 20,</u>
Line 47, insert "wherein" after -- and --.

<u>Column 21,</u>
Line 62, insert "which is the disruptable semi-permeable membrane" after
-- controlling layer --.
Line 63, delete "1)" and substitute therefor -- 2) --.
Line 63, delete "another" and substitute therefor -- a second --.
Line 67, delete "(a) a" and substitute therefor -- (a) the --.

<u>Column 22,</u>
Line 1, insert -- first -- after "comprises a".
Lines 5-6, delete "a water swellable substance" and substitute therefor -- one or more of the water swellable substances --.
Line 7, insert -- which is the disruptable semi-permeable membrane -- after "controlling layer".
Line 9, delete "another" and substitute therefor -- a second --.
Line 64, delete "claims 5, 6" and substitute therefor -- claims 1, 5, 6 --.

UNITED STATES PATENT AND TRADEMARK OFFICE
CERTIFICATE OF CORRECTION

PATENT NO. : 6,610,323 B1
DATED : August 26, 2003
INVENTOR(S) : Lundberg et al.

It is certified that error appears in the above-identified patent and that said Letters Patent is hereby corrected as shown below:

<u>Column 23,</u>
Line 7, delete "constitutes" and substitute therefor -- is --.
Line 9, delete "substance" and substitute therefor -- substances --.
Line 37, insert "first" after -- mixing a --.
Line 45, delete "another" and substitute therefor -- a second --.
Line 56, insert "first" after -- shaping a --.

<u>Column 24,</u>
Line 5, delete "another" and substitute therefor -- a second --.

Signed and Sealed this

Sixteenth Day of March, 2004

JON W. DUDAS
*Acting Director of the United States Patent and Trademark Office*